United States Patent [19]

Van Dyke

[11] Patent Number: 5,332,747
[45] Date of Patent: Jul. 26, 1994

US005332747A

[54] METHOD FOR POTENTIATING PRIMARY DRUGS IN TREATING MULTIDRUG RESISTANT PARASITIC DISEASE CELLS

[75] Inventor: Knox Van Dyke, Morgantown, W. Va.

[73] Assignee: Cancer Biologics of America, Inc., Lexington, Ky.

[21] Appl. No.: 537,481

[22] Filed: Jun. 13, 1990

Related U.S. Application Data

[63] Continuation-in-part of Ser. No. 413,710, Sep. 28, 1989, abandoned, and a continuation-in-part of Ser. No. 413,711, Sep. 28, 1989, Pat. No. 5,025,020.

[51] Int. Cl.$^5$ .............................................. A61K 31/44
[52] U.S. Cl. .................................... 514/280; 514/281; 514/227.8
[58] Field of Search ...................... 514/280, 281, 227.8

[56] References Cited

PUBLICATIONS

Gralla et al. "Toxicology Studies With d-Tetrandrine (NSC-77037), a Plant Alkaloid With Vascular and Lymphotoxic Effects in Dogs and Monkeys." *Cancer Chemotherapy Reports Part 3*, vol. 5, No. 1, Sep. 1974, pp. 79-85.

Department of Pharmacology et al. "A Clinical Study of the Antihypertensive Effect of Tetrandrine." *Chinese Medical Journal*, 92(3): 193-198, 1979.

DeConti, Dr. Ronald C. "Phase I Initial Clinical Studies with d-Tetrandrine." *Procter & Gamble Assoc. Cancer Res.*, 16, 96 (1975).

*Molecular and Biochemical Parasitology*, vol. 38 (1990), pp. 281-290 entitled "Emetine-resistant mutants of *Entamoeba histolytica* overexpress mRNAs for multidrug resistance".

"Reversal of drug resistance in *Trypanosoma cruzi* and *Leishmania donovani* by verapamil" appearing in the *Transactions of the Royal Society of Tropical Medicine and Hygiene*, (1989), vol. 83, pp. 197-198.

*Antimicrobial Agents and Chemotherapy*, Jan. 1988, pp. 96-103 entitled "Inhibitors of Folic Acid Synthesis in the Treatment of Experimental Pneumocystis carinii Pneumonia".

"Effect of Bisbenzylisoquinoline (Biscoclaurine) Alkaloids on Multidrug Resistance in KB Human Cancer Cells," by Shiraishi et al. *Cancer Research*, vol. 47, pp. 2413-2416, May 1. 1987.

"Reversal of Chloroquine Resistance in Plasmodium falciparum by Verapamil," Martin, Oduola and Milhous, *Science*, Feb. 20, 1987, pp. 899-901.

"Biochemical Effects of d-Tetrandrine and Thalicarpine," William A. Creasey, *Biochemical Pharmacology*, vol. 25, pp. 1887-1892, Pergamon Press, 1976.

"Phosphorylation of the $M_R$ 170,000 to 180,000 Glycoproteins Specific to Multidrug-Resistant Tumor Cells: Effects of Verapamil, Trifluoperazine, and Phorbol Esters," by Hamada et al., *Cancer Research*, vol. 47, pp. 2860-2865, Jun. 1, 1987.

"Reversal of Chloroquine Resistance in Falciparum Malaria Independent of Calcium Channels," by Ye and Van Dyke, *Biochemical and Biophysical Research Communications*, vol. 155, No. 1, Aug. 30, 1988.

"Potentiation of Antitumor Activity of Vincristine by the Biscoclaurine Alkaloid Cepharanthine," by Kato and Suzumura, *Journal of the National Cancer Institute*, vol. 79, No. 3, Sep. 1987.

"Multidrug Resistance: Molecular Biology and Clinical Relevance," by Rothenberg and Ling, *Journal of the National Cancer Institute*, vol. 81, No. 12, Jun. 21, 1989.

"Multidrug Resistance in Cancer," Kartner and Ling, *Scientific American*, Mar. 1989.

Merck Index 10th Ed. 9056.
Chem Abstracts #75:59822w Mitscher et al.
Chem Abstracts #108:87627e Dreyfus et al. 1988.
Chem Abstracts #110:132058z Fournet et al. 1988.

*Primary Examiner*—Frederick E. Waddell
*Assistant Examiner*—Russell Travers
*Attorney, Agent, or Firm*—Price, Heneveld, Cooper, DeWitt & Litton

[57] ABSTRACT

The specification discloses a method for enhancing the inhibiting action of drugs against multidrug resistant cells, representing various parasitic diseases, apparently by reversing the glycoprotein "pumps" associated with such cells.

7 Claims, 1 Drawing Sheet

METHOD FOR POTENTIATING PRIMARY DRUGS IN TREATING MULTIDRUG RESISTANT PARASITIC DISEASE CELLS

CROSS-REFERENCE TO RELATED APPLICATION

This patent application is a continuation-in-part of U.S. patent application Ser. No. 07/413,710 filed Sep. 28, 1989, now abandoned, and entitled METHOD FOR POTENTIATING PRIMARY DRUGS IN TREATING MULTIDRUG RESISTANT CELLS, and is a continuation-in-part of U.S. patent application Ser. No. 07/413,711 filed Sep. 28, 1989, now U.S. Pat. No. 5,025,020, entitled USE OF TETRANDRINE AND ITS DERIVATIVES TO TREAT MALARIA.

BACKGROUND OF THE INVENTION

The present invention relates to the treatment of multidrug resistance in certain parasitic diseases. In addition to having been observed in malaria, multidrug resistance is a phenomenon which has been observed in other parasitic diseases such as Entamoeba histolytica (amoebic dysentery), Trypanosoma (African sleeping sickness), Leishmania and AIDS pneumonia.

A number of diverse drugs have been found effective against such diseases. However in many cases, the initial success of physicians in treating the disease is followed by total failure. Drugs which worked initially become totally ineffective after a period of time. An initial period of remission is often followed by a period of frustration during which nothing seems to be effective against the disease. Death becomes inevitable.

Such multidrug resistance in cancer cells has been associated with an increase in the drug resistant cell in the presence of 150,000 to 170,000 molecular weight glycoproteins in the drug resistant cell. Such P150-170 Kd glycoproteins act as a drug exit pump, to pump disease fighting drugs out of the infected or infecting cells which the drugs are supposed to kill. This glycoprotein pump phenomenon in cancer cells has been reported in a March 1989 *Scientific American* article by Kartner and Ling. (No concession is made that this publication is prior art as to subject matter contained in the parent applications.) The presence of a very similar glycoprotein pump in drug resistant malaria has also been discovered by the inventor.

It has been reported by Rothenberg and Ling that multidrug resistance in cancer can be reversed by using hydrophobic molecules with two planar aromatic rings and a tertiary basic nitrogen atom with a positive charge at physiologic pH. *Journal of the National Cancer Institute*, Vol. 81, No. 12, Jun. 21, 1989, on page 907. (No concession is made that this publication is prior art.) A representative compound of this class, and indeed apparently a major member of this class which has actually been the subject of experimental work is the drug verapamil, whose structural formula is shown below:

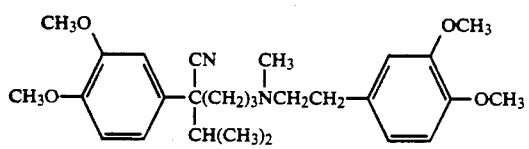

Verapamil is a calcium channel blocker. Other researchers have claimed that calcium channel blockers are effective against malaria. However while such results may be substantiatable in vitro, they have little practical value as clinical treatments in vivo. While calcium channel blockers are therapeutic in the treatment of hypertension at moderate levels, they are toxic at levels high enough to effect MDR reversal.

Another technique for MDR reversal in cancer which is of laboratory interest but which has no practical applicability involves inducing point mutations of the energy related ATP binding sites in the glycoprotein. Such point mutations result in an almost complete loss of MDR activity, according to Rothenberg and Ling, supra. While such in vitro work is important, it lacks in vivo clinical applicability.

Shiraishi et al. disclose work on the use of cepharanthine to treat multidrug resistance in cancer. Isotetrandrine, tetrandrine, fangchinoline and herbamine are said to show similar effects in cancer. Anti-tumor effects of tetrandrine have also been mentioned.

Researchers throughout the world continue to press for techniques for reversing multidrug resistance. A successful clinical technique for reversing multidrug resistance will be one of the most important breakthroughs in the fight against parasitic diseases exhibiting the multidrug resistance phenomenon.

SUMMARY OF THE INVENTION

The present invention involves the use of methoxadiantifoline, tetrandrine and certain of its derivatives to potentiate the effectiveness of a primary drug against particular drug resistant parasitic disease cells. The method of the present invention appears to reverse the glycoprotein pump of a multidrug resistant cell so that such a resistant cell actually accepts a greater concentration of drug than a so-called drug sensitive cell.

DESCRIPTION OF THE PREFERRED EMBODIMENT

Figure 1:
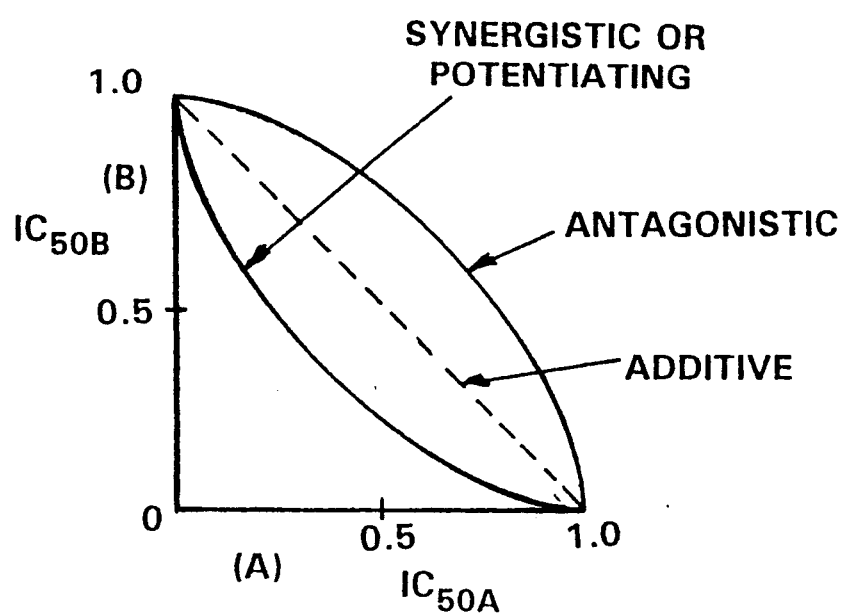
FIG. 1 illustrates an isobologram of drawings A and B.

In the preferred embodiment, the tetrandrine like compounds of the present invention have the following structural formula:

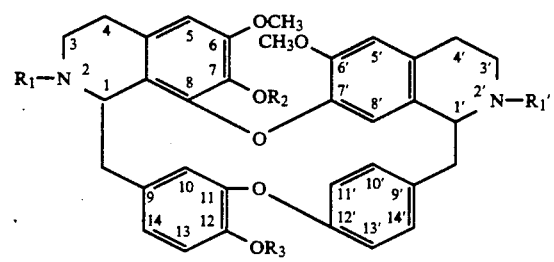

where $R_1$ and $R_1'$ are the same or different shortchained carbon based ligand including with limitation, $CH_3$, $CO_2CH_3$ or H; and $R_2$ is $CH_3$; and $R_3$ is $CH_3$ or hydrogen; and has the "S" isomeric configuration at the C-1' chiral carbon location.

Not all members of the tetrandrine family of compounds operate to enhance or potentiate the activity of a primary drug against a multidrug resistant cell. Only those members of the family having the specific configuration outlined above are are operable in this manner. Of the eight representative members of the family above, only tetrandrine, isotetrandrine, hernandezine and herbamine act to potentiate the primary drug against multidrug resistant cells.

In addition to these specific members of the tetrandrine family, it has been found that methoxadiantifoline also potentiates the effectiveness of a primary drug against a multidrug resistant cell. These compounds actually make the drug resistant cell more sensitive to the inhibitory action of a drug than is the so-called drug sensitive cell. At present, the only logical explanation for this result is that the method of the present invention actually involves reversing or inhibiting the glycoprotein pumps which are found in greater abundance on drug resistant cells. Thus the glycoprotein pump mechanism which originally made the cell multidrug resistant to drug inhibition actually works against the cell in the present invention to make the cell more sensitive to drug inhibition.

The tetrandrine family of compounds as a whole includes tetrandrine, isotetrandrine, hernandezine, herbamine, pycnamine, phaeanthine, obamegine and fangchinoline, which list is not intended to be exhaustive. In all of these examples, $R_1$ and $R_1'$ constitute the methyl group. Variation within the group occurs in that $R_2$ and $R_3$ may constitute either a methyl group or hydrogen, and the isomeric configuration of the compounds at the C-1 and C-1' chiral carbon positions is either R (rectus) or S (sinister). The rules for R and S configuration can be found in Morrison and Boyd, "Organic Chemistry," 4th Edition, copyright 1983 by Allyn and Bacon, at pages 138-141. In addition, hernandezine includes a methoxy group at the C-5 position, a substitution which does not appear to be significant in the operability of the compound in the present invention. The specific manner in which these exemplary family members vary is set forth in Table V below, wherein these family members are compared to two nonfamily members for activity against drug sensitive and drug resistant strains of *P falciparum* malaria.

A specific in vivo dosage for each of the various compounds used in the present invention has not been established. However, such dosage can be established through routine clinical experimentation by referencing the concentrations at which the various compounds have exhibited 50% inhibition as set forth in Tables I through V herein. These concentrations have been from about 0.1 to about 3 micro molar. Such concentrations can be achieved in vivo by administering dosages of from about 100 to about 300 mg/day. It is known that at these concentrations, tetrandrine is substantially nontoxic. The preferred method for administering the drug is orally, though other methods such as injection may be used.

In the treatment of various parasitic diseases, a member of the tetrandrine family as described above or methoxadiantifoline, or mixtures thereof, is administered in conjunction with primary drugs known to have effectiveness against the parasitic disease. In the treatment of malaria, the tetrandrine or methoxadiantifoline is preferably combined with chloroquine or qinghaosu. This combination is claimed generically in one of the parent applications referenced above and is claimed specifically for the treatment of malaria in another of the parent applications referenced above.

Trypanosomiasis is caused in humans by trypanosoma cruzi, gambiense and rhodesiense, and in cattle by congolense. For treating Trypanosomiasis, a preferred primary drug used in combination with a tetrandrine, as described above, or methoxadiantifoline, or combinations thereof, is nifurtimox.

Leishmania is caused by Leishmania donovani, tropica and brasiliensis (brasiliensis). A preferred primary drug used in combination with a tetrandrine, methoxadiantifoline or combinations of the foregoing, is antimony.

Amoebic dysentery is caused by Entamoeba histolytica, an enteric protozoan parasite. A preferred primary drug to be combined with a tetrandrine, methoxadiantifoline or any combination of the foregoing, in the treatment of amoebic dyscentery is Emetine.

The active parasite in AIDS pneumonia is Pneumocystis carinii. Pneumocystis carinii has long been recognized as an important opportunistic pulmonary pathogane. It is especially virulent and dangerous in AIDS' patients. The preferred primary drugs to be used in combination with a tetrandrine, methoxadiantifoline or any combination of the foregoing include: trimethoprim, diaveridine, pyrimethamine, tetroxoprim, pitrexim, and trimetrexate, sulfonamides and sulfones, including sulfamethoxasole, sulfadiazine, sulfadoxine, sulfamonomethoxine, dapsone, and sulfonylbisformanilide.

The effectiveness of tetrandrine in potentiating antimalarial drugs in multidrug resistant parasitic malarial cells was determined by comparing the antimalarial action of tetrandrine and chloroquine alone and in combination against a *P falciparum* malarial strain which is sensitive to chloroquine and another which is resistant to chloroquine. A similar study was conducted using tetrandrine and qinghaosu. Chloroquine and qinghaosu are commonly used antimalarial drugs.

The dose ($IC_{50}$) of each drug or each drug combination required to effect a 50% inhibition in the malarial activity of each strain was determined by establishing a dose response curve for each.

FCMSU1/Sudan strain and cloned Indochina (W-2) strain of *P falciparum* were used. The former is sensitive to chloroquine and the latter is resistant to chloroquine. The two strains of the parasite were cultured according to the candle jar method of Trager and Jensen, *Science*, Vol. 193, pages 673–675 (1976). In a given experiment, four-day-old Petri dish cultures (approximately 10% parasitemia) were diluted with medium containing an amount of noninfected type A human erythrocytes to obtain a culture with a final hematocrit of 1.5% and parasitemia of 0.5–1.0%. The resulting culture was ready for addition to microtitration plates with ninety-six flat-bottom wells.

The testing procedure used was similar to that described by Desjardins et al. in "Antimicrobial Agents and Chemotherapy," Vol. 16, pages 710–718 (1979). Briefly, the final volume added to each of the ninety-six well microtitration plates was 250 ul and consisted of 25 ul of complete medium with or without the primary drug (chloroquine or qinghaosu), 175 ul of either the parasitized culture or a nonparasitized human erythrocyte control, and 25 ul of complete medium with or without tetrandrine. 25 ul radioactive (0.5 uCl) [2,8-$^3$H] adenosine. The microtitration plates were incubated in a candle jar for an additional 18 hours, at 37° C.

As the malaria parasite grows $^3$H-adenosine is metabolized and incorporates into polymeric RNA and DNA. The labeled polymers are trapped on glass fiber filters and unincorporated material is washed away. In the absence of drug there is 100% incorporation of the labeled material. When drugs interfere (directly or indirectly), an inhibitory dose of 50% (IC$_{50}$) can be calculated. The experiments were repeated three times except where noted. Statistical analysis was done using Student's T-test for significance. Van Dyke et al. "Exp. Parasitol," Vol. 64, pages 418-423 (1987).

When tetrandrine is added to chloroquine, it supplements and potentiates the antimalarial activity. When tetrandrine is added to qinghaosu or chloroquine, it provides long-acting and synergistic activity to qinghaosu or chloroquine. This can be seen in Tables I-IV. Remarkably, when 3.0 u molar tetrandrine is added to 0.1 u molar chloroquine, the IC$_{50}$ of chloroquine can be lowered 43-Fold.

the x axis. The combinations of drug A and drug B are mixed and tested that are below IC$_{50}$ of either drug and the points are located on the graph. If the two drugs are additive, there is a straight line between the Y$_1$X0 (drug B) and Y$_0$X$_1$ (drug A). If the line or curve bends below the straight line, the drugs are synergistic or potentiating. If the line bends above the straight line, the two drugs are antagonistic.

TABLE 2

IC$_{50}$ (nM) OF TT AND QHS FOR EACH DRUG ALONE AND IN COMBINATION*

| MALARIA** | SINGLE DRUG | | DRUG COMBINATION** | | |
|---|---|---|---|---|---|
| | TT | QHS | TT (1.0 uM) QHS (0.3 uM) | TT (2.0 uM) QHS (0.2 uM) | TT (3.0 uM) QHS (0.1 uM) |
| S STRAIN | 410.2 ± 69.0 | 36.7 ± 4.7 | 71.9 ± 8.9 (TT) 21.6 ± 2.7 (QHS) | 113.5 ± 6.3 (TT) 11.4 ± 0.6 (QHS) | 219.5 ± 35.5 (TT) 7.3 ± 1.2 (QHS) |
| R STRAIN | 205.6 ± 49.8 | 47.8 ± 14.5 | 59.6 ± 13.7 (TT) 17.9 ± 4.1 (QHS) | 71.8 ± 13.8 (TT) 7.2 ± 1.4 (QHS) | 136.9 ± 41.6 (TT) 4.6 ± 1.4 (QHS) |

*The data in the table above are the mean values ± S.D (nM) from three experiments except where noted.
**Ratios of TT/QHS in the drug combinations are 10:3, 10:1 and 30:1 respectively.
***S and R strains represent CQ-sensitive (FCMSU1/Sudan) and resistant (W2) strain of P. falciparum respectively

TABLE 1

IC$_{50}$ (nM) OF TT AND CQ FOR EACH DRUG ALONE AND IN COMBINATION*

| MALARIA*** | SINGLE DRUG | | DRUG COMBINATION** | | |
|---|---|---|---|---|---|
| | TT | CQ | TT (1.0 uM) CQ (0.3 uM) | TT (2.0 uM) CQ (0.2 uM) | TT (3.0 uM) CQ (0.1 uM) |
| S STRAIN | 498.1 ± 93.7 | 26.7 ± 3.8 | 54.9 ± 7.1 (TT) 16.5 ± 2.1 (CQ) | 114.1 ± 23.0 (TT) 11.4 ± 2.3 (CQ) | 223.3 ± 38.6 (TT) 7.4 ± 1.3 (CQ) |
| R STRAIN | 197.5 ± 24.7 | 185.8 ± 4.9 | 79.5 ± 13.7 (TT) 23.8 ± 4.1 (CQ) | 79.5 ± 16.1 (TT) 8.0 ± 1.6 (CQ) | 124.6 ± 9.6 (TT) 4.2 ± 0.3 (CQ) |

*The data in the table above are the mean values ± S.D (nM) from three experiments except where noted.
**Ratios of TT/CQ in the drug combinations are 10:3, 10:1 and 30:1 respectively.
***S and R strains represent CQ-sensitive (FCMSU1/Sudan) and resistant (w2) strain of P. talciparum respectively When the inhibiting activity of two drugs, e.g., A and B are compared, the middle point of the dose response curve is usually chosen as the basis for comparison. This point is known as the inhibitory dose that occurs at the point of 50% inhibition of the response to be measured (inhibitory concentration at 50% inhibitory response=IC$_{50}$). As illustrated in FIG. 1, an isobologram is developed by comparing the IC$_{50}$ of one drug against the other, i.e., drug A against drug B. We start by putting the IC$_{50}$ of drug B at the top of the y axis marked 1.0. The IC$_{50}$ of drug A is placed at the position 1.0 on

TABLE 3

EFFECT OF COMBINATION OF TETRANDRINE AND CHLOROQUINE ON P. FALCIPARUM

| MALARIA** | TRIAL | SFIC* | | |
|---|---|---|---|---|
| | | 1.0 uM TT 0.3 uM CQ | 2.0 uM TT 0.2 uM CQ | 3.0 uM TT 0.1 uM CQ |
| S STRAIN | 1 | 0.77 | 0.66 | 0.73 |
| | 2 | 0.64 | 0.77 | 0.70 |
| | 3 | 0.78 | 0.55 | 0.75 |
| | MEAN ± S.D | 0.73 ± 0.06 | 0.66 ± 0.09 | 0.73 ± 0.02 |
| R STRAIN | 1 | 0.60 | 0.45 | 0.74 |
| | 2 | 0.68 | 0.63 | 0.76 |
| | 3 | 0.36 | 0.30 | 0.50 |
| | MEAN ± S.D | 0.55 ± 0.14 | 0.46 ± 0.14 | 0.67 ± 0.12 |

*SFIC represents sum of fractional inhibitory concentration as described by Berenbaum (11), SFIC is equal to one in cases of additive effects of the drugs, higher than one in cases of antagonism and lower than one in synergistic action.
**S and R strain: chloroquine sensitive (FCMSU1/Sudan) and resistant (w2) strain of P. falciparum.

TABLE 4

EFFECT OF COMBINATION OF TETRANDRINE AND QINGHAOSU ON P. FALCIPARUM

| MALARIA** | TRIAL | SFIC* | | |
|---|---|---|---|---|
| | | 1.0 uM TT 0.3 uM QHS | 2.0 uM TT 0.2 uM QHS | 3.0 uM TT 0.1 uM QHS |
| S STRAIN | 1 | 0.77 | 0.68 | 0.71 |
| | 2 | 0.74 | 0.49 | 0.72 |
| | 3 | 0.79 | 0.62 | 0.77 |
| | MEAN ± S.D | 0.77 ± 0.02 | 0.60 ± 0.08 | 0.73 ± 0.03 |
| R STRAIN | 1 | 0.63 | 0.46 | 0.71 |
| | 2 | 0.77 | 0.72 | 0.74 |
| | 3 | 0.64 | 0.40 | 0.81 |

TABLE 4-continued

EFFECT OF COMBINATION OF TETRANDRINE AND QINGHAOSU ON *P. FALCIPARUM*

| MALARIA** | TRIAL | SFIC* | | |
|---|---|---|---|---|
| | | 1.0 uM TT 0.3 uM QHS | 2.0 uM TT 0.2 uM QHS | 3.0 uM TT 0.1 uM QHS |
| | MEAN ± S.D | 0.68 ± 0.06 | 0.52 ± 0.14 | 0.75 ± 0.04 |

*SFIC represents sum of fractional inhibitory concentrations as described by Berenbaum (11), SFIC is equal to one in cases of additive effects of the drugs, higher than one in cases of antagonism and lower than one in synergistic action.

**S and R strain: chloroquine sensitive (FCMSU1/Sudan) and resistant (W2) strains of *P. falciparum*.

In an attempt to explain this surprising result, tetrandrine and various of its derivatives and several nontetrandrine derivatives were tested for their individual effectiveness against a chloroquine sensitive and a chloroquine resistant strain of *P falciparum malaria*. The test procedure was basically the same as outlined above. The nonfamily members were cycleanine, cepharanthine, methoxadiantifoline and thalicarpine, whose structural formulas are illustrated herebelow:

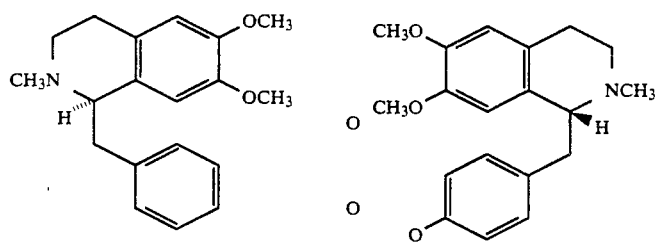

Structure of cycleanine

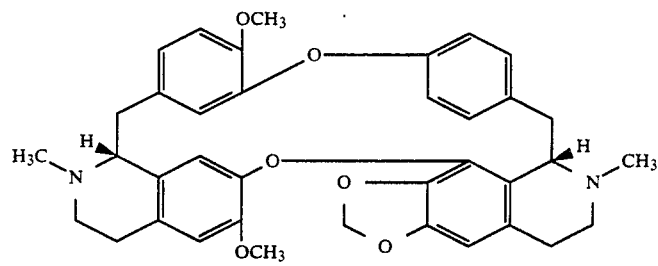

Structure of cepharanthine.

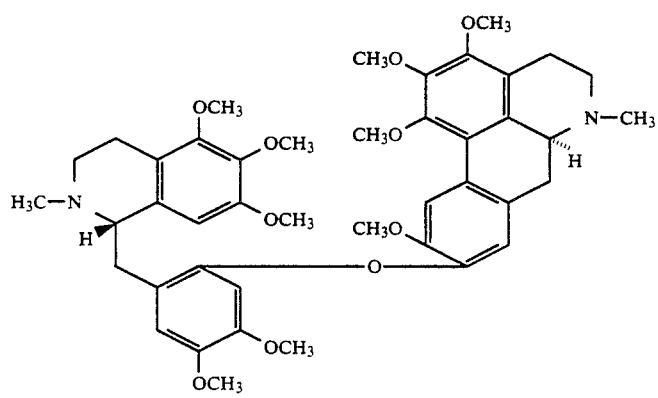

METHOXADIANTIFOLINE

-continued

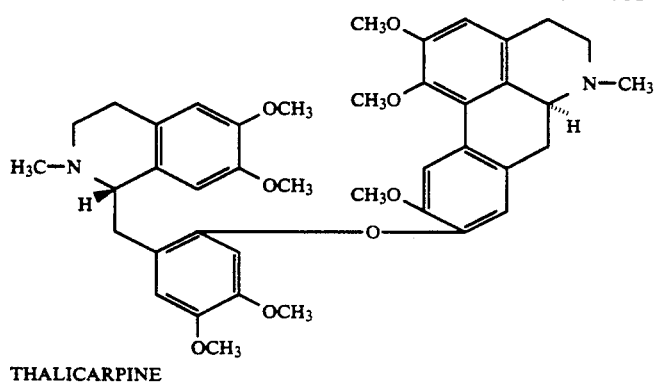

THALICARPINE

These comparative activities are set forth in Table V below.

changes and alterations can be made without departing from the spirit and the broader aspects thereof.

| CHEMICAL STRUCTURE ANTIMALARIAL ACTIVITY OF BISBENZYL ISOQUINOLINE ALKALOIDS AGAINST *PLASMODIUM FALCIPARUM* IN VITRO | | | | | | | | | |
|---|---|---|---|---|---|---|---|---|---|
| Drug | Configuration | | Substituents | | | | Oxygen | $IC_{50} (10^{-7}M)$ | Ratio |
| (a) | C-1 | C-1' | C-5 | C-7 | C-12 | C-5' | Bridge | S'''' R'''' | (S/R)'' |
| TT | S | S | H | OCH3 | OCH3 | | C8–C7' C11–C12' | 2.9  1.2 | 2.6 |
| IT | R | S | H | OCH3 | OCH3 | | C8–7' C11–C12' | 4.8  1.4 | 3.5 |
| HE | S | S | OCH3 | OCH3 | OCH3 | | C8–C7' C11–C12' | 3.7  1.3 | 2.8 |
| BB | R | S | H | OCH3 | OH | | C8–C7' C11–C12' | 4.6  1.9 | 2.7 |
| PY | R | R | H | OCH3 | OH | | C8–C7' C11–C12' | 3.8  4.2 | 0.9 |
| PH | R | R | H | OCH3 | OCH3 | | C8–C7' C11–C12' | 6.0  5.0 | 1.2 |
| OB | R | S | H | OH | OH | | C8–C7' C11–C12' | 6.6  4.8 | 1.5 |
| FA | S | S | H | OH | OCH3 | | C8–C7' C11–C12' | 2.6  2.2 | 1.2 |
| CY | R | R | H | OCH3 | | | C8–C12' C12–C8' | 32  42 | 0.8 |
| CE | S | R | H | OCH2— | | | C8–C7' C12–C11' | 10  9.4 | 1.1 |
| ME | S | S | OCH3 | OCH3 | OCH3 | OCH3 | C10–C12' | 53  9.7 | 5.5 |
| TH | S | S | H | OCH3 | OCH3 | H | C10–C12' | 17  13 | 1.3 |

(a): TT-tetrandrine; IT-isotetrandrine; HE-hernandezine; BB-berbamine; PY-pycnamine; PH-phacanthine; OB-obamegine; FA-fangchinoline; CY-cycleanine; CE-cepharanthine; ME-methoxadiantifoline; TH-thalicarpine ''$IC_{50}$ of a drug against sensitive strain of *P. falciparum* is devided by $IC_{50}$ for resistant strain.

''''S and R represent chloroquine-sensitive and resistant strain of *P. falciparum*.

The results of Table V illustrate that methoxadiantifoline and those members of the tetrandrine family having the "S" isomeric configuration at the C-1' chiral carbon and having at least one of the R2 substituent comprising CH3 are actually substantially more effective against the chloroquine resistant malarial strain than against the chloroquine sensitive malarial strain. This extremely surprising result suggests that these compounds actually reverse or inhibit the pumping action of the glycoprotein associated with such multidrug resistant cells. Instead of pumping the toxic drug out of the cell, it actually appears to be pumping a lesser concentration of the toxic drug out of the cell. At present, this is the only reasonable explanation for these surprising results, since the only known significant difference between the multidrug resistant cells and the corresponding drug sensitive cells is the substantially greater percentage of P-glycoprotein associated with the multidrug resistant cell.

Of course it is understood that the above is merely a preferred embodiment of the invention and that various changes and alterations can be made without departing from the spirit and the broader aspects thereof.

The embodiments of the invention in which an exclusive property or privilege is claimed are defined as follows:

1. A method for potentiating a primary drug to treat cell multidrug resistance in Trypanosoma comprising:
    exposing multidrug resistant Trypanosoma cells to effective concentrations of a compound having the following formula:

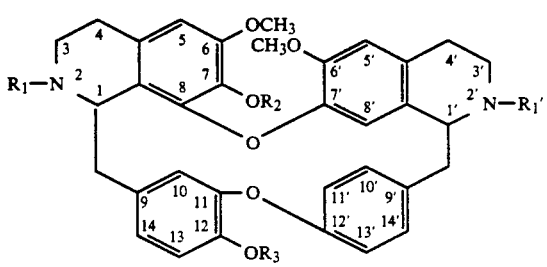

wherein $R_1$ and $R_1'$ are the same or different short chained carbon based ligand; $R_2$ is $CH_3$ is and $R_3$ is $CH_3$ or hydrogen, and the isomeric configuration at the C-1' chiral carbon location is "S" and at least one of $R_2$ and $R_3$ comprises $CH_3$.

2. The method of claim 1 in which said compound comprises tetrandrine.

3. The method of claim 2 in which said compound is used at a dosage level of from about 100 to 300 mg per day.

4. The method of claim 3 wherein the use of said compound is combined with the use of at least one principal drug known to be effective for treating Trypanosoma.

5. The method of claim 4 in which said drug comprises nifurtimox.

6. The method of claim 1 wherein the use of said compound is combined with the use of at least one principal drug known to be effective for treating Trypanosoma.

7. The method of claim 6 in which said drug comprises nifurtimox.

* * * * *

UNITED STATES PATENT AND TRADEMARK OFFICE
CERTIFICATE OF CORRECTION

PATENT NO. : 5,332,747
DATED : July 26, 1994
INVENTOR(S) : Knox Van Dyke

It is certified that error appears in the above-indentified patent and that said Letters Patent is hereby corrected as shown below:

Column 3, Line 4:

"herbamine" should be --berbamine--.

Column 3, Lines 22-23:

"herbamine" should be --berbamine--.

Signed and Sealed this

Twenty-eight Day of February, 1995

Attest:

BRUCE LEHMAN

*Attesting Officer*  *Commissioner of Patents and Trademarks*